United States Patent [19]

Kataoka et al.

[11] Patent Number: 4,925,534
[45] Date of Patent: May 15, 1990

[54] HEMODIALYSIS METHOD AND MEMBRANE

[75] Inventors: Hiroshi Kataoka; Tetsunosuke Kunitomo, both of Kamakura; Takuichi Kobayashi, Shiga, all of Japan

[73] Assignee: Toray Industries Inc., Japan

[21] Appl. No.: 278,814

[22] Filed: Dec. 2, 1988

Related U.S. Application Data

[62] Division of Ser. No. 59,548, Jun. 8, 1987, Pat. No. 4,834,882.

[30] Foreign Application Priority Data

Jun. 13, 1986 [JP] Japan ................................ 61-136125
Jun. 30, 1986 [JP] Japan ................................ 61-151679

[51] Int. Cl.$^5$ ............................................. B01D 13/00
[52] U.S. Cl. ................................. 210/647; 210/500.35
[58] Field of Search ............ 210/647, 646, 645, 321.64, 210/500.35, 317

[56] References Cited

U.S. PATENT DOCUMENTS 4,059,512 11/1977 Harris ..................................... 210/24
4,212,744 7/1980 Oota ................................. 210/321.64

FOREIGN PATENT DOCUMENTS 57-56039 4/1982 Japan .

OTHER PUBLICATIONS

EP-A-0012630, published 06/25/80, Masahiro et al.

Primary Examiner—Frank Spear
Attorney, Agent, or Firm—Austin R. Miller

[57] ABSTRACT

This invention provides method and membrane for hemodialysis which has a total protein permeability of not more than 0.2%, and has a reduction rate of $\beta_2$-microglobulin of not less than 5%. The hemodialysis membrane of the present invention selectively removes $\beta_2$-microglobulin which was shown to cause some long-term complications such as carpal tunnel syndrome in the patients undergoing hemodialysis, while preventing the leakage of useful proteins.

9 Claims, No Drawings

HEMODIALYSIS METHOD AND MEMBRANE

This is a division of application Ser. No. 059,548 filed June 8, 1987, now Pat. No. 4,834,882.

BACKGROUND OF THE INVENTION

1. Field of the Invention

This invention relates to a method and membrane which removes $\beta_2$-microglobulin from blood in a hemodialysis procedure. More particularly, this invention relates to a membrane which selective remove $\beta_2$-microglobulin when blood is purified by hemodialysis.

2. Description of the Prior Art

Long-term complications have been found to occur in patients undergoing hemodialysis for blood purification. These complications include osteopathy, anemia and carpal tunnel syndrome. Although countermeasures against these disorders have long been studied, they have been largely relatively ineffective. The belief is now spreading that some blood components cannot be removed or are not significantly removed by current hemodialysis procedures typically conducted by using a cellulosic membrane, and that they remain and accumulate in the blood and participate in causing long-term complications. However, these components have not yet been completely identified and even their participation in the complications has not yet been proved. The present inventors first proved that the carpal tunnel syndrome, from which patients undergoing hemodialysis often suffer, is caused by the deposition of amyloid fibers, and that a component of the amyloid fibers is $\beta_2$-microglobulin (Biochem. Biophys. Res. Commun. 129, pp. 701-706, 1985).

Heretofore, it has been attempted to remove uremic large and medium size molecules by using a dialysis membrane which permits the passage of proteins, instead of using a typical dialysis membrane which does not allow proteins to pass through. A number of such membranes have been developed. However, these membranes are used for the purpose of non-selectively removing uremic large molecules, and accordingly in some cases more than 20 g of proteins the removed in one dialysis. When such a membrane is continuously used there is a serious danger than the patient may develop hypoproteinemia.

SUMMARY OF THE INVENTION

We have discovered that $\beta_2$-microglobulin is not significantly removed by conventional hemodialysis and that it accumulates in patients undergoing hemodialysis to the extent of 20 to 100 times more than normal subjects. We have discovered that it is very important to remove significant amounts of $\beta_2$-microglobulin from the blood of patients undergoing hemodialysis.

An important object of the present invention is to provide a procedure which effectively and selectively removes significant quantities of $\beta_2$-microglobulin from blood while preventing leakage of undue amounts of useful proteins such albumin.

The foregoing and other objects are accomplished by the present invention which provides a method and a membrane for hemodialysis, wherein significant quantities of $\beta_2$-microglobulin are removed from the blood along with other impurities, without removing significant quantities of desirable proteins. This is accomplished by performing dialysis through a membrane which has a total protein permeability of not more than 0.2% and a $\beta_2$-microglobulin reduction rate of not less than 5%.

DETAILED DESCRIPTION OF THE PREFERRED EMBODIMENTS

The term "total protein permeability" herein means the quotient expressed in terms of percentage, which quotient is obtained by dividing the means protein level in the dialysate by the total protein level in the blood before dialysis, when conducted under conditions of 200 ml/min. of blood flow and 500 ml/min. of dialysate flow. The term "mean protein level in dialysate" means the average level of the total proteins in the dialysate obtained after 1 and 4 hours from commencement of dialysis. The protein level in the blood is determined by using the Biuret method, and that in the dialysate is determined by using the Kingsbury-Clark method. The total protein permeability must be not more than 0.2%. If it is higher than 0.2%, about 20 g of proteins are lost in one dialysis, and hypoproteinemia may be caused. Thus, the total protein permeability should be not more than 0.2%, preferably not more than 0.1%, and still more preferably not more than 0.05% in order continuously to use the membrane without any clinical problem.

The term "reduction rate of $\beta_2$-microglobulin" as used herein means the quotient expressed in terms of percentage, which quotient is obtained by division of a numerator by a denominator; the numerator is the difference obtained by subtracting the level of $\beta_2$-microglobulin in the blood after dialysis from that before dialysis, and the denominator is the $\beta_2$-microglobulin level in the blood before dialysis. The $\beta_2$-microglobulin level in the blood is determined by the RIA method. When this value becomes 5% or more, the $\beta_2$-microglobulin level in the blood of the patient starts to decrease. One of the major objects of the hemodialysis in many cases is to remove water accumulated in the body of the patient because the patient excretes only limited amounts of urine, so that the blood is condensed typically by 20 to 30%, and sometimes by as much as 40%. Therefore, the $\beta_2$-microglobulin percentage in the blood after dialysis includes an increased level due to hemoconcentration of the blood. Thus, a 5% reduction rate of $\beta_2$-microglobulin actually means that about 20 to 30% of $\beta_2$-microglobulin is removed. Although a higher reduction rate of $\beta_2$-microglobulin in generally better than a lower rate, an excessively high rate may cause excessive loss of useful proteins. Accordingly the upper limit of reduction rate may be about 50%. The preferred reduction rate of $\beta_2$-microglobulin in the present invention is not less than 10%, and more preferably not less than 15%.

The hemodialysis membrane of the present invention has an effective pore radius determining the permeability of the membrane to various substances. In this invention the pore radius of the pores in the active layer of the membrane is 4 to 15 nm, preferably 4 to 10 nm, and more preferably 5.5 to 9.5nm.

The hemodialysis membrane of the present invention preferably has a total volume porosity of 35 to 75%, and preferably has a pore volume porosity of 25% or more.

The pore size of the active layer means, in cases of uniform membranes, the average pore radius, while in cases of asymmetrical membranes such as those composed of a support layer and a tight inner surface, it means the average pore radius in the inner surface.

In general, if the pore radius is larger than the equivalent radius of $\beta_2$-microglobulin in the blood, the elimination of $\beta_2$-microglobulin is mainly due to permeation. In this case, the danger of causing hypoproteinemia is increased since the pore radius is similar to the equivalent radii of other useful proteins. The conventional so-called protein permeable membranes are categorized in this group.

If the pore radius is small, needless to say, $\beta_2$-microglobulin is rejected on the surface of the membrane, so that it cannot pass through the membrane. Conventional typical dialysis membranes are examples of this problem.

If the pore radius is in the intermediate range, that is, if the pore radius is slightly larger than the equivalent radius of $\beta_2$-microglobulin, the $\beta_2$-microglobulin can enter the inner portion of the membrane through the membrane surface. The surface of a membrane made with a high polymer material of the type usually used for the dialysis has a tendency to adsorb proteins in the membrane body. Therefore, $\beta_2$-microglobulin entities which entered the membrane are trapped by adsorption on the inner surfaces of the pores of the membrane. As a result, a portion of the $\beta_2$-microglobulin is transferred from the blood to the membrane, depending on the effective adsorption area, and is accordingly removed from the blood. Since the $\beta_2$-microglobulin which has entered the pore in the membrane is successively adsorbed on the inner wall, the initial concentration gradient is always kept. Thus, the rate of transfer is kept high avoiding the decrease with time. Thus, it is important that the membrane shall have an optimum structure in terms of pore radius, inner surface area and number of pores.

Another problem is presented if the pore radius is too large, in addition to the above-mentioned problem of permeation of proteins. Many more portions of the membrane become plugged with high molecular weight proteins, so that the invasion and adsorption of $\beta_2$-microglobulin is hindered. Since a portion of the $\beta_2$-microglobulin remains trapped in the membrane matrix and another portion of the $\beta_2$-microglobulin permeates the membrane and accumulates in the dialysate, the amount of $\beta_2$-microglobulin removed cannot be determined only by analyzing the dialysate.

The hemodialysis membrane of the present invention has a very effective membrane structure for removal of $\beta_2$-microglobulin, from the viewpoint of both adsorption and permeations.

In cases where the membrane material has a chemical adsorption affinity for $\beta_2$-microglobulin, the amount of adsorbed $\beta_2$-microglobulin is sharply increased when the pore radius is in the pore radius range of this invention. The critical pore radius range to $\beta_2$-microglobulin is about 4 nm. That is, if the pore radius is less than 4 nm, the effectiveness of the membrane for removal of $\beta_2$-microglobulin is limited, but if the pore radius is 4 nm or more, invasion and entrapment of $\beta_2$-microglobulin in the membrane occur, so that the reduction rate is increased. If the pore radius is 15 nm or more, especially 20 nm or more, $\beta_2$-microglobulin removal is governed by permeation and the permeation of other proteins is also increased. This is disadvantageous in view of the danger of causing hypoproteinemia.

In cases where the membrane is a symmetrical membrane, the pore radius of the dialysis membrane of the present invention is determined based on the DSC (Differential Scanning Calories) method by measuring the lowering of freezing point due to the capillary condensation of the water in the pores ("Membranes and Membrane Processes" p 507, Plenum Press, New York, 1986). In cases where the membrane is an asymmetrical membrane, pore radius can be determined based on the pore theory by conducting the water permeation test as described in "Membranes and Membrane Processes", p. 507, Plenum Press, New York, 1986.

The DSC method utilizes the phenomenon that the freezing point of water varies depending on the pore radius. In this method, after removing water from the inner and outer surfaces of a hollow fiber sample, tens of fibers of about 5 mm length are packed in a pan. The pan is sealed, weighed and tested in a differential scanning calorimeter ("DSC-2C", manufactured by Perkin-Elmer). After freezing the sample at $-45°$ C., the sample is heated at a rate of 2.5° C./min. and the measurement is conducted.

By conducting the DSC measurement as mentioned above, a melting curve having a peak depending on the pore radius may be obtained. For example, if the pore radius is 15 nm, a melting curve with a peak at $-1.1°$ C. is obtained, so that the pore radius may be easily determined.

The membrane of the present invention preferably has a total volume porosity $V_t$ (%) of 35 to 75%, and a pore volume porosity $V_P$ (%) of at least 25%, which porosities are defined by the equation set forth below.

After obtaining the above-mentioned melting curve, the heat of fusion ($\Delta H_P$) is obtained from the area sandwiched between the melting curve in the region of not higher than $-1.1°$ C. and the base line. The amount of pore water $W_P$ is obtained from the heat of fusion of water $\Delta H_m$ (79.7 cal/g) as follows:

$$W_P = \Delta H_P / \Delta H_m$$

Further, total amount of water $W_T$ is determined by the absolute drying method. Using these measured values, the total volume porosity $V_T$(%) and pore volume porosity $V_P$(%) are defined by the following equation:

$$\text{Total Volume Porosity } V_T (\%) = \frac{W_T}{W_T + M_P/\rho_P} \times 100$$

$$\text{Pore Volume Porosity } V_P (\%) = \frac{W_P}{W_T + M_P/\rho_P} \times 100$$

where
$W_T$: Total Amount of Water (g) (Absolute Drying MEthod)
$M_P$: Polymer Weight (g) (Ditto)
$\rho_P$: Specific Gravity of Polymer
$W_P$: Amount of Pore Water (g)

In general, to provide practical permeability as a dialysis membrane, the membrane preferably has a total volume porosity $V_T$ of at least 35%. However, a membrane having a total volume porosity of more than 75% is disadvantageous because the strength of the membrane is low and it is likely to break under the stresses exerted during manufacture or use.

A pore volume porosity of at least 25% is preferred because it gives sufficient effective adsorption area for $\beta_2$-microglobulin. If the total volume porosity $V_T$ is in the preferred range of 35 to 75% and the $V_P$ is less than 25%, the percentage of large pores with a radius of 15 nm or more is 10 to 50%, so that the leakage of useful proteins such as albumin is considerable. Further, water permeability is also disadvantageously abnormally increased to make it difficult to control the water count, and the fluctuation of inorganic salts and electrolytes in the body fluid is too great and is disadvantageous.

Turning now to the materials constituting the hemodialysis membranes of the present invention, high polymers typically used for hemodialysis or hemofiltration may be used. More specifically, non-limiting examples of these materials include polymethylmethacrylate, polyacrylonitrile, cellulose, cellulose acetate, polysulfone, polyvinyl alcohol and polyvinyl alcohol copolymers such as copolymers of vinyl alcohol and ethylene. The preferred materials includes polymethylmethacrylate and cellulose acetate, and the most preferably materials include polymethylmethacrylate. The form of the membrane module is not limited; it may be in the form of, for example, hollow fibers or multiple layers of flat membranes.

To obtain the advantageous of the present invention by dissolving the above-mentioned high polymer is a solvent for the polymer, and spinning the polymer by extruding the solution from a spinneret having an annular extrusion orifice into an aqueous coagulation bath, the concentration of the polymer in the solution, the cooling conditions in the coagulation and solidification steps, and the rate of desolvation should be controlled. For example, when a membrane is prepared in the form of a hollow fiber using a polymethylmethacrylate-based polymer as the material of the membrane, the polymer is dissolved in a solvent such as dimethylsulfoxide to a polymer concentration of 15% by weight to 30% by weight. In preparing a hollow fiber by extruding the solution from a spinneret having an annular extrusion orifice, dry nitrogen gas is blown to the inside of the hollow fiber and cooling gas is blown to the outside of the hollow fiber. The cooling gas is preferred to have a dry-bulb temperature of 15° to 17° C., and to have a dew point, which is an indicator of its water content, of 5° to 15° C. Then the fiber is introduced into a water-based coagulation bath to solidify and desolvate the fiber. The coagulation bath preferably has a temperature of 5° to 30° C.

The present invention will now be further described with respect to specific illustrative examples.

EXAMPLE 1

Fifteen parts of isotactic polymethylmethacrylate polymerized using a Grignard reagent and 75 parts of syndiotactic polymethylmethacrylate produced by radical polymerization were dissolved in 260 parts of dimethylsulfoxide to obtain a spinning solution. This spinning solution was extruded from the outer portion of a spinneret having an annular extrusion orifice while blowing moist air having a temperature of 13° C. to form hollow fibers. The fibers were coagulated and desolvated in water at 10° C. to obtain hollow fibers having inner diameters of 245 μm and outer diameters of 305 μm. Seventy five hundred of the fibers were bundled to obtain a module with an effective surface area of 1.0 m². The membrane structure was categorized as a uniform membrane and the means pore radius was 7.2 nm. The pore volume porosity (hereinafter simply referred to as $V_P$) was 42%, and the total volume porosity (hereinafter simply referred to as $V_T$) was 62%.

Clinical tests were conducted using the dialyzer for one month. The average of its total protein permeability was 0.017% and the average protein loss in one dialysis was 1.5 g. The dialyzer was used without any problem. The reduction rate of $\beta_2$-microglobulin was 17% on the average, and the $\beta_2$-microglobulin level in the blood of the patient undergoing the dialysis was significantly reduce. Thus clear clinical effect and improvement was established.

COMPARATIVE EXAMPLE 1

A spinning solution similar to the spinning solution used in Example 1, but having a different composition of 12 parts of isotactic polymethylmethacrylate, 52 parts of syndiotactic polymethylmethacrylate and 240 parts of dimethylsulfoxide was extruded from an outer extruding hole of a spinneret having an annular extrusion orifice to obtain hollow fibers while introducing dry nitrogen gas to the inner sides of the fibers and blowing moist air at a temperature of 20° C. to the outsides of the fibers. The fibers were coagulated and desolvated in water at 26° C., and a module was prepared as in Example 1. The mean pore radius was 16 nm, $V_P$ was 35%, and $V_1$ was 81%.

The thus obtained dialyzer was clinically tested. Although the reduction rate of $\beta_2$-microglobulin was as high as 50%, the total protein permeability was 0.25% and the protein loss in one dialysis was as much as 23 g. Since hypoproteinemia was expected, the test was stopped.

COMPARATIVE EXAMPLE 2

A spinning solution similar to the spinning solution used in Example 1, but having a different composition of 12 parts of isotactic polymethylmethacrylate, 60 parts of syndiotactic polymethylmethacrylate and 240 parts of dimethylsulfoxide was extruded from an outer extruding hole of a spinneret having an annular extrusion orifice to obtain hollow fibers while introducing dry nitrogen gas to the inner sides of the fibers and blowing moist air at a temperature of 0° C. to the outsides of the fibers. The fibers were coagulated and desolvated in water at 10° C., and a module was prepared as in Example 1. The mean pore radius was 3.2 nm, $V_P$ was 52%.

The thus obtained dialyzer was subjected to a clinical test. Although the total protein permeability was very low and did not present a problem, the reduction rate of $\beta_2$-microglobulin was as low as 2.2% and the $\beta_2$-microglobulin in the blood was hardly reduced. Thus no significant clinical effect was shown.

EXAMPLE 2

Fifteen parts of diacetylcellulose with an acetyl value of 42% was dissolved in 85 parts of dimethylformamide to obtain a spinning solution. This spinning solution was extruded from an outer extruding hole of a spinneret having an annular extrusion orifice to form fibers while introducing an aqueous dimethylformamide solution to the inner sides of the fibers. The fibers were coagulated and desolvated in water at 12° C. to obtain fibers having inner diameters of 245 μm and outer diameters of 365 μm. A module with an effective surface area of 1.0 m² was prepared from the hollow fibers. The mean pore radius was 8 nm, $V_P$ was 35% and $V_T$ was 50%.

The thus prepared dialyzer was subjected to a dialysis procedure where a model blood was circulated into the blood compartment of the dialyzer. The total protein permeability was 0.02%, and the average level of $\beta_2$-microglobulin in the dialysate was substantially identical as in Example 1. Thus, a clinical effect was expected to be obtained.

the results obtained are shown in Table 1. It can be seen that the amount of absorbed $\beta_2$-microglobulin is low if the pore radius is 4 nm or less.

TABLE 1

| | Material of Dialysis Membrane | Pore Radius (nm) | $V_P$ (%) | $V_T$ (%) | $C_I$ (mg/l) | $C_L$ (mg/l) | $C_D$ (mg/l) | Adsorption Amount (mg) |
|---|---|---|---|---|---|---|---|---|
| Example 3 | Polymethylmethacrylate | 7.2 | 42 | 62 | 56 | 29 | 0.76 | 0.20 |
| Comparative Example 3 | Polymethylmethacrylate ("B2-100") | 2.0 | 26 | 51 | 56 | 47 | 0.01 | 0.07 |
| Example 4 | Ethylene Vinyl Alcohol | 3.0 | 27 | 48 | 56 | 45 | 2.10 | 0.04 |
| Example 5 | Cellulose Acetate | 3.5 | 22 | 48 | 56 | 40 | 3.48 | 0.06 |

EXAMPLE 3, COMPARATIVE EXAMPLES 3 TO 5

Thirty six hollow fibers were taken from the $\beta_2$-microglobulin-removing hemodialysis module obtained in Example 1, and the fibers were stuffed into a glass tube having an inlet nozzle and an outlet nozzle for the dialysate. Both ends of the fibers were sealed with an epoxy resin and the edge surfaces thereof were cut to open the hollow fibers. Both ends of the fibers were provided with a polyvinyl chloride tube to make a small dialyzer. The effective surface area was 30 cm². Eight milliliters of blood plasma from a patient undergoing dialysis, in which the $\beta_2$-microglobulin level was 56 mg/l, were circulated in the hollow fibers at a flow rate of 0.64 ml/min. From the dialysate inlet of the glass tube module, 3.5 ml of a dialysate (a solution containing 7g/l of sodium chloride was 0.5 g/l of sodium nitride in a phosphate buffer (pH 7.4) (as defined in the Japanese Pharmacopoeia) was introduced and the module was sealed. The dialysate was exchanged every 20 minutes, and this procedure was repeated 6 times. The level of $\beta_2$-microglobulin ($C_D$ mg/l) in each of the used dialysates was determined by the RIA method using a kit commercially available from Pharmacia. The $\beta_2$-microglobulin level after the procedure ($C_L$ mg/l)) was also determined.

The amount of $\beta_2$-microglobulin permeated into the dialysate was calculated from the $C_D$ value for each of the 6 runs. The amount of the $\beta_2$-microglobulin removed from the plasma was shown by the difference between the initial value $C_I$ and $C_L$ value.

The amount of $\beta_2$-microglobulin adsorbed in the membrane was calculated by subtracting the amount of $\beta_2$-microglobulin permeated into the dialysate from the amount removed from the plasma. The results are shown in Table 1.

The same procedure was repeated with different standard membranes: a polymethylmethacrylate membrane (trade name "B2-100", manufactured by Toray Industries Inc.), an ethylene vinyl alcohol membrane (trade name "KF-201-12C", manufactured by Kuraray Co., Ltd.), and a cellulose acetate membrane (trade name "Duoflux", manufactured by CD Medical), and

We claim:

1. In a method of purifying the blood of a patient, wherein said blood contains desirable proteins along with impurities including $\beta_2$-microglobulins and wherein said blood is subjected to the action of a dialysis membrane which removes impurities from the blood, the steps which comprise:
   (a) subjecting said blood to a dialysis procedure controlled to remove impurities but to retain desirable proteins in the blood,
   (b) controlling the dialysis to cause removal from the blood of $\beta_2$-microglobulin at a reduction rate of 5% or more while impeding significant losses of said desirable proteins, and
   (c) said membrane having a total protein permeability of 0.2% or less, a $\beta_2$-microglobulin reduction rate of 5% or more, a total volume porosity of 35 to 75% and a pore volume porosity of 25% or more, said membrane including an active layer portion having pore radii of 4–15 nm.

2. The method defined in claim 1, wherein said membrane is porous and the pore radius of the pores in its active layer is 4 nm to 10 nm.

3. The method defined in claim 1, wherein said membrane is porous and the pore radius of the pores in its active layer is 5.5 nm to 0.5 nm.

4. The method defined in claim 1, wherein said reduction rate is about 5–50%.

5. The method defined in claim 1, wherein said reduction rate is about 10–50%.

6. The method defined in claim 1, wherein said reduction rate is about 15–50%.

7. The method of claim 1 wherein the material constituting the dialysis membrane is selected from the group consisting of polymethylmethacrylate, polyacrylonitrile, cellulose, cellulose acetate, polysulfone, polyvinyl alcohol and a copolymer of vinyl alcohol and ethylene.

8. The method of claim 7, wherein the material constituting the dialysis membrane is polymethylmethacrylate.

9. The method of claim 7, wherein the material constituting the dialysis membrane is cellulose acetate.

* * * * *